(12) United States Patent
Wimmer

(10) Patent No.: US 7,850,604 B2
(45) Date of Patent: Dec. 14, 2010

(54) FLEXIBLE SHAFT FOR AN ENDOSCOPE AND SUCH AN ENDOSCOPE

(75) Inventor: Viktor Wimmer, Seeon (DE)

(73) Assignee: Karl Storz GmbH & Co. KG (DE)

( * ) Notice: Subject to any disclaimer, the term of this patent is extended or adjusted under 35 U.S.C. 154(b) by 1426 days.

(21) Appl. No.: 11/282,805

(22) Filed: Nov. 18, 2005

(65) Prior Publication Data

US 2006/0111617 A1    May 25, 2006

(30) Foreign Application Priority Data

Nov. 19, 2004    (DE) .................. 10 2004 057 481

(51) Int. Cl.
*A61B 1/005* (2006.01)
(52) U.S. Cl. .................... 600/139; 600/144
(58) Field of Classification Search .............. 600/139, 600/140, 144, 129, 130; 267/89, 90, 105, 267/284, 287
See application file for complete search history.

(56) References Cited

U.S. PATENT DOCUMENTS

| | | | | |
|---|---|---|---|---|
| 3,082,438 | A * | 3/1963 | Nachman, Jr. ............... | 267/91 |
| 4,329,980 | A | 5/1982 | Terada ........................ | 128/4 |
| 4,669,172 | A | 6/1987 | Petruzzi ...................... | 29/456 |
| 4,977,887 | A | 12/1990 | Gouda ......................... | 128/4 |
| 5,363,882 | A * | 11/1994 | Chikama ..................... | 138/118 |
| 5,704,926 | A * | 1/1998 | Sutton ......................... | 604/526 |
| 5,873,866 | A * | 2/1999 | Kondo et al. ................ | 604/526 |
| 6,083,152 | A * | 7/2000 | Strong ......................... | 600/139 |
| 6,186,483 | B1 * | 2/2001 | Bullard ........................ | 267/89 |
| 6,485,411 | B1 | 11/2002 | Konstorum et al. ......... | 600/139 |
| 7,044,921 | B2 * | 5/2006 | Asmus et al. ................ | 606/192 |
| 7,052,489 | B2 * | 5/2006 | Griego et al. ................ | 606/1 |
| 2002/0002323 | A1 | 1/2002 | Moriyama ................... | 600/140 |
| 2002/0022825 | A1 * | 2/2002 | Saitou et al. ................. | 604/525 |
| 2005/0059861 | A1 * | 3/2005 | Nishiie ......................... | 600/144 |
| 2005/0165275 | A1 * | 7/2005 | Von Felten et al. .......... | 600/140 |
| 2007/0270649 | A1 * | 11/2007 | Long ............................ | 600/144 |

FOREIGN PATENT DOCUMENTS

| | | |
|---|---|---|
| DE | 697 23 193 | 5/2004 |
| DE | 10 2004 057 481 | 5/2006 |
| EP | 0 835 637 | 7/2003 |
| WO | WO 96/09009 | 3/1996 |

OTHER PUBLICATIONS

European Search Report; Mar. 4, 2006; 3 pages.

* cited by examiner

*Primary Examiner*—John P Leubecker
*Assistant Examiner*—Victoria W Chen
(74) *Attorney, Agent, or Firm*—St. Onge Steward Johnston & Reens LLC

(57) ABSTRACT

A flexible shaft for an endoscope comprises a shaft body which, in the longitudinal direction of the shaft, has a first portion with a first degree of flexibility, and, proximally from the first portion, has at least a second portion with a second degree of flexibility which is less than the first degree of flexibility, the shaft body having, in the first portion, at least a first spring element, and, in the second portion, at least a second spring element. A spring hardness of the second spring element is increased by a permanent pretensioning of the second spring element, as a result of which the flexibility of the shaft body is reduced in the second portion.

7 Claims, 4 Drawing Sheets

FLEXIBLE SHAFT FOR AN ENDOSCOPE AND SUCH AN ENDOSCOPE

CROSS REFERENCE TO RELATED APPLICATION

The present application claims priority of German application No. 10 2004 057 481.2 filed Nov. 19, 2004.

BACKGROUND OF THE INVENTION

The invention relates to a flexible shaft for an endoscope, comprising a shaft body which, in the longitudinal direction of the shaft, has a first portion with a first degree of flexibility, and, proximally from the first portion, has at least a second portion with a second degree of flexibility which is less than the first degree of flexibility, the shaft body having, in the first portion, at least a first spring element, and, in the second portion, at least a second spring element.

The invention also relates to an endoscope comprising a flexible shaft of the aforementioned type.

An endoscope comprising a flexible shaft is also referred to as flexible endoscope. Flexible endoscopes are used mainly for medical applications, but the present invention can also be applied to flexible endoscopes that can be used for technical purposes, for example for inspection of machinery.

Flexible endoscopes differ from rigid endoscopes in that the shaft of a flexible endoscope is of such flexibility that it can adopt a bent, strongly curved or even coiled configuration.

Flexible endoscopes of this kind are therefore suitable in particular as endoscopes for medical operations or examinations in internal body regions with branched or looped structures, for example in the gastrointestinal tract or in the airways, including the lungs.

A flexible endoscope used to examine the large intestine, in some cases with the possibility of performing a biopsy and conducting minor surgical interventions, is also called a colonoscope.

A flexible endoscope also has the characteristic that the distal end portion of the flexible shaft has still further increased mobility and flexibility so that this distal end portion, which is also called "deflecting" can be deflected, i.e. bent away from the longitudinal direction of the rest of the shaft, by means of a control device. Generally, the distal end portion can be deflected in a plane to both sides of the rectilinear setting, for example in an angle range of more than ±90°. The control device provided for deflecting the distal end portion is arranged at the proximal end of the flexible shaft and normally comprises a manually operated actuating element which is operatively connected to the distal end portion via a traction cable mechanism, so that the operating physician can suitably alter and adjust the deflection of the distal end portion to the particular requirements. The deflection of the distal end portion permits a large number of viewing directions through the endoscope.

While a high degree of flexibility of the shaft of a flexible endoscope is desired in the deflecting distal end portion, a lesser degree of flexibility, i.e. a greater stiffness of the flexible shaft, is desired in the proximal area of the endoscope shaft. The reason for this is that the flexible shaft as a whole can have a considerable length. When pushing the endoscope forwards, for example in the intestine of a patient, the pushing force must not cause the shaft to arch in the proximal area. If the shaft archs during insertion into the intestine, or even archs along with the intestine, this causes painful looping of the intestine. In other words, during insertion, the shaft of the endoscope must remain as straight as possible in the proximal area, which, in the proximal area, and despite guaranteed flexibility, requires a certain stability or a tendency of the shaft to automatically straighten out again in the event of arching.

The flexible shaft for an endoscope known from the document U.S. Pat. No. 6,485,411 comprises a shaft body constructed from a plurality of integrally connected spring elements in the manner of helical springs. The individual turns of the spring elements consist of a band-like flat material, the turns having a defined width in the longitudinal direction of the shaft.

The shaft body of this known flexible shaft has at least three portions with different degrees of flexibility. A distal portion has the highest degree of flexibility, i.e. is the most flexible; the next portion adjoining it has a lesser degree of flexibility by comparison; and the portion adjoining the latter proximally has a still lesser degree of flexibility. This known shaft accordingly has a flexibility that decreases in stages from distal to proximal.

In this known shaft, the different degrees or stages of flexibility are obtained by the fact that the width of the individual turns of the spring elements increases from distal to proximal, as a result of which the degree of flexibility decreases from distal to proximal. The document describes, however, how the different degrees of flexibility can also be obtained with equal widths of the turns in the longitudinal direction of the shaft, by different spacings between adjacent turns of the individual spring elements, which spacings, on production of the spring elements, are formed by the axial width of the material removed between the turns.

In a shaft body designed in this way, it has been found that, over the course of time, after a large number of applications, it shows signs of fatigue, and these result in an increased and undesired play of the control device for deflecting the distal end portion of the shaft. In this way, exact positioning of the endoscope in the examination or treatment area in the human body is made difficult.

It has also been found that a flexible shaft of this kind, especially in the proximal area, loses its stability as a result of the alternating loads arising during insertion and removal of the endoscope, i.e. the flexibility increases in the proximal area. This in turn leads undesirably to a situation where the pushing force applied during insertion causes the shaft to arch or buckle in the proximal area, because the tendency of the shaft to automatically straighten itself diminishes over the course of time through fatigue of the spring elements. This fatigue of the shaft body in the proximal area also has an effect on the outer jacket which surrounds the shaft body and which usually consists of a plastic tube, to the extent that the latter is inclined to crease and tear.

In contrast to that, the flexible shaft known from the document U.S. Pat. No. 4,329,980 comprises a flexible cylindrical hollow tube and a single helical spring, an end of which can be engaged with an end of the cylindrical hollow tube, whereby the flexibility of the flexible shaft can be adjusted. To this end, a mechanism for compressing the helical spring is provided at the other end of the cylindrical hollow tube, which mechanism comprises a slider which engages with the other end of the single helical spring, as well as an actuating portion for a to-and-fro-movement of the element for compressing the spring between a position in which the element for compressing the spring compresses the single helical spring, and a position, in which the element for compressing the spring is axially spaced apart from the end of the helical spring. Thus, the axial compression of the windings of the helical spring is adjustable with this flexible shaft.

The complexity and thus, cost expensive design of the slider drive for compression the helical spring is a disadvantage of this known flexible shaft.

Further, from document DE 697 23 193 C2, a treatment forceps for use with an endoscope is known, which comprises a flexible shaft made up from a closely wound stainless steel coil. The shaft comprises a portion which is easier to be bent than the remaining portion. This different degree of flexibility of the shaft is achieved by a pretension of the one portion of the stainless steel coil, wherein the pretension is such that adjacent windings of the coil are in contact with one another in order to increase the rigidity.

SUMMARY OF THE INVENTION

The object of the invention is to develop a flexible shaft for an endoscope of the type mentioned at the outset, such that the aforementioned disadvantages are avoided, in particular such that the flexibility of the shaft body in the second position is reduced in a constructively simple fashion.

According to an aspect of the invention, a flexible shaft for an endoscope is provided, comprising a shaft body extending in a longitudinal direction, and having in the longitudinal direction a first portion with a first degree of flexibility, and, proximally from the first portion, at least a second portion with a second degree of flexibility which is less than the first degree of flexibility, the shaft body having, in the first portion, at least a first spring element, and, in the second portion, at least a second spring element, at least the second spring element being constructed from helical windings, a spring hardness of the second spring element being increased by a permanent pretensioning of the second spring element, as a result of which the second degree of flexibility of the shaft body is reduced in the second portion, the pretensioning of the second spring element being applied by an axial compression of the windings relative to one another, the pretensioning being applied by a traction element pulling the windings of the second spring element axially together.

In the flexible shaft according to the invention, the reduction in the flexibility of the shaft body in the second portion is achieved by a permanent pretensioning of the second spring element. The second spring element is thus under permanent pretensioning which has the effect of stabilizing the shaft in the direction of its longitudinal axis, i.e. the tendency of the second portion of the shaft to resist arching, or to automatically straighten again after deflection, is increased by the permanent pretensioning of the second spring element. This inventive configuration of the shaft body at least in the second portion does not therefore derive from the known measure of increasing the spring hardness of the spring element by increasing the width of the turns in the axial direction, but instead involves pretensioning, as a result of which the shaft is less susceptible to fatigue under the alternating loads which act on the spring element.

In this connection, at least the second spring element is constructed from helical windings, and the pretensioning is applied by an axial compression of the windings relative to one another.

In this configuration, at least the second spring element, like the shaft body of the known shaft, is constructed from a helical spring, but the greater spring hardness of the second spring element is not obtained by widening the windings or turns in the axial direction, but by compression of the helical spring. This also has the advantage of easier production of different spring hardnesses, since the first portion and the second portion, for example, can be formed from, and indeed preferably configured as, a total of one spring element, and the portion of the spring element forming the second portion of the shaft body is permanently compressed. A shaft body with at least two portions of different degrees of flexibility is in this way particularly easy to produce, without having to use two spring elements whose turns or windings have different geometries. The compression can be so strong that adjacent windings touch.

The pretensioning is applied by a traction element which pulls the second spring element axially together.

Such a traction element, which can be configured for example in the form of one or more traction wires or traction cables, has the advantage that it can be easily connected to the second spring element, for example by a known connecting technique such as welding, soldering or adhesive bonding.

It is preferred in this connection, if the traction element is secured on the second spring element only at two axially separate sites, the distance between them corresponding to the length of the second spring element in the compressed state.

The advantage of this is that the relative mobility of the spring element with respect to the traction element between the two points of attachment of the traction element on the second spring element is maintained, which is significant for the function of the second spring element, namely it can easily deflect in each direction, which is important for a flexible endoscope.

In a further preferred embodiment, the traction element is a net-like sleeve element surrounding the second spring element.

Such a net-like sleeve element, which for example consists of a metal net, also has the advantage of protecting the spring element or spring elements of the shaft body. Moreover, a net-like sleeve element of this kind, particularly in connection with the aforementioned embodiment in which the sleeve element is secured on the second spring element only at two axially separate sites, makes it possible for the second spring element to move by sliding along the inner wall of the net-like sleeve element. The sleeve element also advantageously contributes to the shaft's resistance to twisting.

It is preferred if the sleeve element extends substantially along the entire length of the shaft body.

The advantage of this is that the outer contour of the flexible shaft can be made flat, i.e. free from projections and irregularities.

The use of a net-like material also has the advantage that this can be pulled particularly easily onto the spring elements, which further simplifies the production of the shaft, and only a few attachment points have to be provided for fixing the sleeve element along the length of the shaft body.

In another preferred embodiment, the sleeve element is surrounded by an outer jacket which is firmly connected to the sleeve element.

Such an outer jacket, which is preferably made from plastic, advantageously has the effect, in conjunction with the sleeve element, that the flexible shaft as a whole can be made rigid with respect to twisting, so that rotation movements of the shaft about its longitudinal axis do not lead to twisting of the shaft. The connection between the outer jacket and the sleeve element is preferably a form-fit connection, for example with the outer jacket being connected to the net-like sleeve element under the action of heat.

In another preferred embodiment, the first spring element and the at least second spring element are formed integrally with one another.

The advantage of this is that the number of parts needed for construction of the shaft body is reduced. In particular, the first spring element and the at least second spring element can be formed as portions of one and the same spring element, so that, as has already been described, the spring hardness of the second portion of this spring element is increased by the permanent pretensioning with respect to the rest of the spring element.

In another preferred embodiment, the shaft body has at least a third portion with a third degree of flexibility, the shaft body having a third spring element in the third portion, the third degree of flexibility being greater than the first degree of flexibility and greater than the second degree of flexibility.

In this embodiment, the flexible shaft has at least three portions with different degrees of flexibility, where the at least third portion with the at least third spring element preferably forms the distal end of the portion since it has the least spring hardness. In contrast to the prior art, however, the pretensioning of the second spring element, as provided for by the invention, means that only two spring elements with different geometries are needed to achieve three different degrees of flexibility, since the second degree of flexibility is achieved by a pretensioning of the second spring element.

In this connection, it is in turn preferred if the first, second and at least third spring element are formed integrally with one another.

In this embodiment, even in the case of an at least three-stage flexible shaft, the production cost is advantageously kept down.

In another preferred embodiment, the first spring element and the second spring element have the same spring hardness in the non-pretensioned state of the second spring element.

This measure also advantageously contributes to the easier production of the shaft according to the invention, because the first spring element and the second spring element can first be produced as portions of one and the same one-piece spring element, after which one portion of this one-piece spring element is subjected to pretensioning, as a result of which this pretensioned portion acquires a greater spring hardness than the remaining portion of the spring element.

According to another aspect of the invention, an endoscope is provided which comprises a flexible shaft according to one or more of the aforementioned embodiments.

Further advantages and features will become clear from the following description and from the attached drawing.

It will be appreciated that the features mentioned above, and those still to be discussed below, can be used not only in the respectively cited combinations, but also in other combinations or singly, without departing from the scope of the present invention.

BRIEF DESCRIPTION OF THE DRAWINGS

An illustrative embodiment of the invention is shown in the drawing and is described in more detail below with reference to said drawing, in which.

DETAILED DESCRIPTION OF A PREFERRED EMBODIMENT

Figure 1:
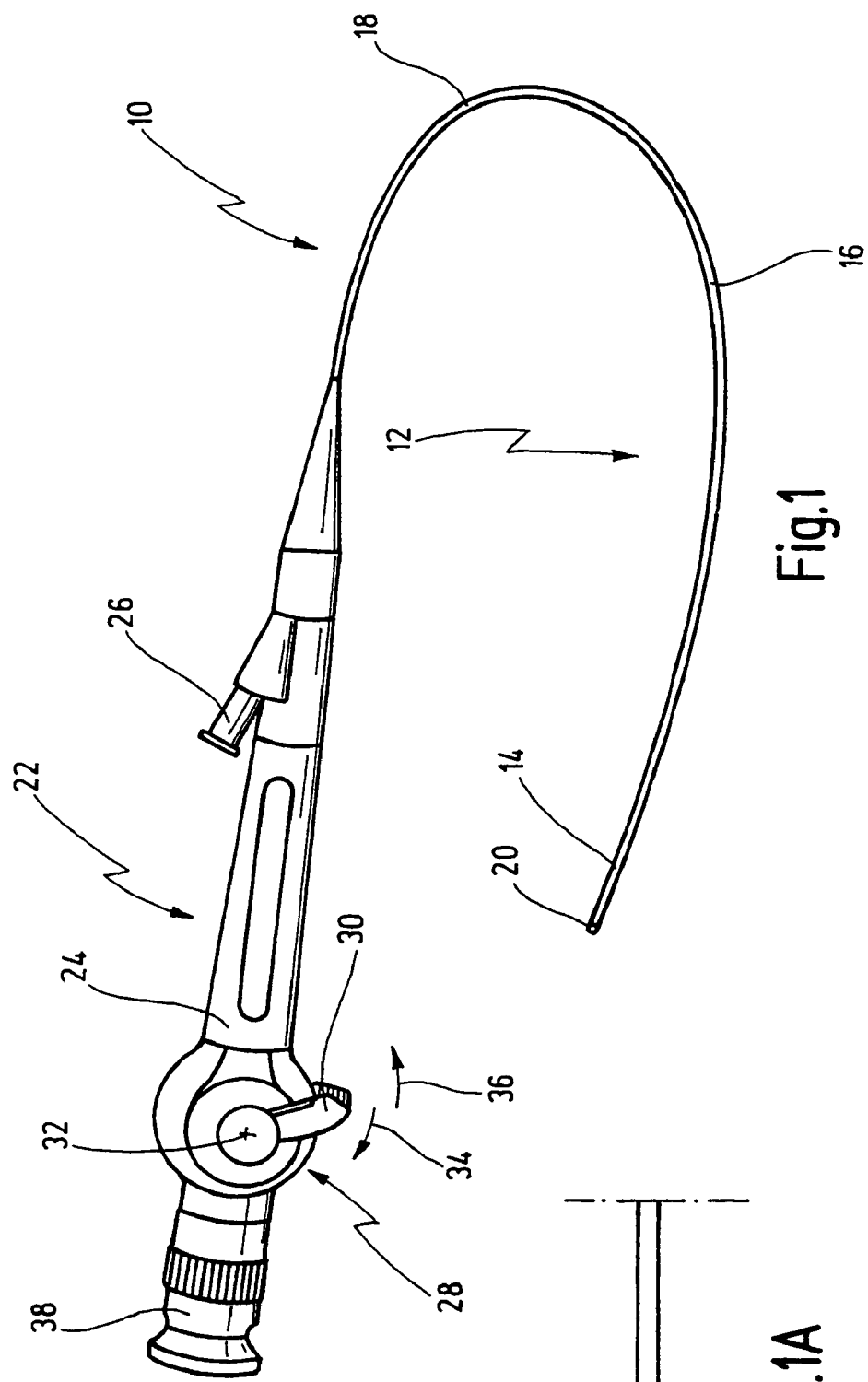
FIG. 1 shows a general view of an endoscope with a flexible shaft.

In FIG. 1, a flexible endoscope is generally labelled by reference number 10. The endoscope 10 is used for examination purposes and/or for operating purposes in medical procedures. The endoscope 10 is, for example, a colonoscope.

The endoscope 10 has an elongate, flexible shaft 12 which will be described in detail later. An endoscope optics system (not shown) in the form of light guide fibres runs through the shaft 12, and possibly also various channels, such as a suction and irrigation channel and, if appropriate, an instrument channel. In the case of a colonoscope, the shaft is longer than it is for a bronchoscope.

The flexible shaft 12 has a distal portion 14, a central portion 16 and a proximal portion 18. The outermost distal end of the distal portion 14 has an endpiece 20 in the form of a closure bushing.

At its proximal end, the shaft 12 is connected to a headpiece 22 which comprises a housing 24.

At the distal end of the headpiece 22, a connector 26 is fitted on the housing 24 for the purpose, for example, of inserting an instrument into the aforementioned instrument channel of the shaft 12.

Figure 1A:
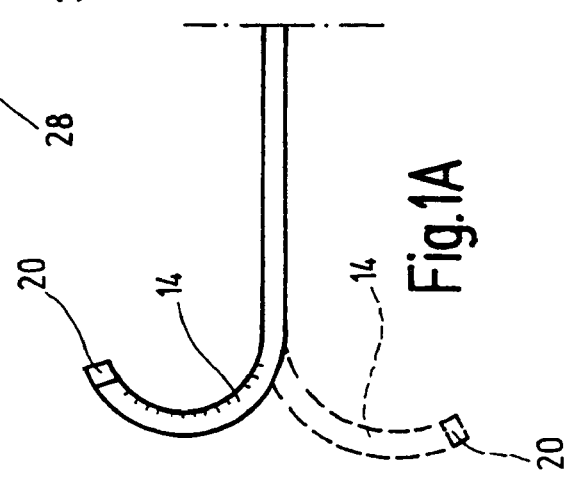
FIG. 1A shows a distal end of the shaft of the endoscope from FIG. 1.

As is shown in FIG. 1A, the distal portion 14 of the shaft 12 can be deflected in two directions from the rectilinear setting shown in FIG. 1, a deflection of the portion 14 from the rectilinear setting being possible in both directions by almost 180° or even up to 210°. In the case of a colonoscope, the distal portion 14 can be deflected in four directions.

To deflect the distal portion 14 from the rectilinear setting, a traction cable mechanism (not shown) is provided which is operatively connected to a control device 28 on the headpiece 22 so that, by actuating the control device 28, the distal portion 14 can be deflected.

The control device 28 is in this case a manually operated control device with an actuating element 30 in the form of a swivel lever which can be swivelled about a rotation axis 32. If the actuating element 30 is swivelled in the direction of an arrow 34 about the rotation axis 32, the distal portion 14 according to FIG. 1A is deflected or curved in one direction, as is indicated by solid lines in FIG. 1A, and, by moving the actuating element 30 in the direction of an arrow 36, the distal potion 14 is deflected or curved in the opposite direction, as is indicated by broken lines in FIG. 1A.

An eyepiece 38 is also arranged at the outer proximal end of the headpiece 22.

The design of the shaft 12 is described in more detail below with reference to FIGS. 2 to 4.

The shaft 12 has a shaft body 40 comprising a first portion 42, which corresponds to the central portion 16 in FIG. 1, a second portion 44, which corresponds to the proximal portion 18 in FIG. 1, and a third portion 46, which corresponds to the distal portion 14.

In the three portions 42 to 46, the shaft body 40 in each case has a different degree of flexibility, the flexibility of the shaft body 40 being greatest in the distal third portion 46, i.e. in this area the shaft body 40 is at its most flexible.

In the first portion 42, which is arranged proximally from the third portion 46 in the longitudinal direction, the flexibility of the shaft body 40 is less than in the third portion 46, and, in the second portion 44, which adjoins the first portion 42 proximally, the flexibility of the shaft body 40 is less than in the portion 46 and also less than in the portion 42.

In each of the portions 42, 44 and 46, the shaft body 40 has a spring element, specifically a third spring element 48 in the third portion 46, a first spring element 50 in the first portion 42, and a second spring element 52 in the second portion 44.

The spring elements 48 to 52 are designed in the form of helical springs and each have a plurality of helical turns or windings 54, 56 and 58.

Figure 3:
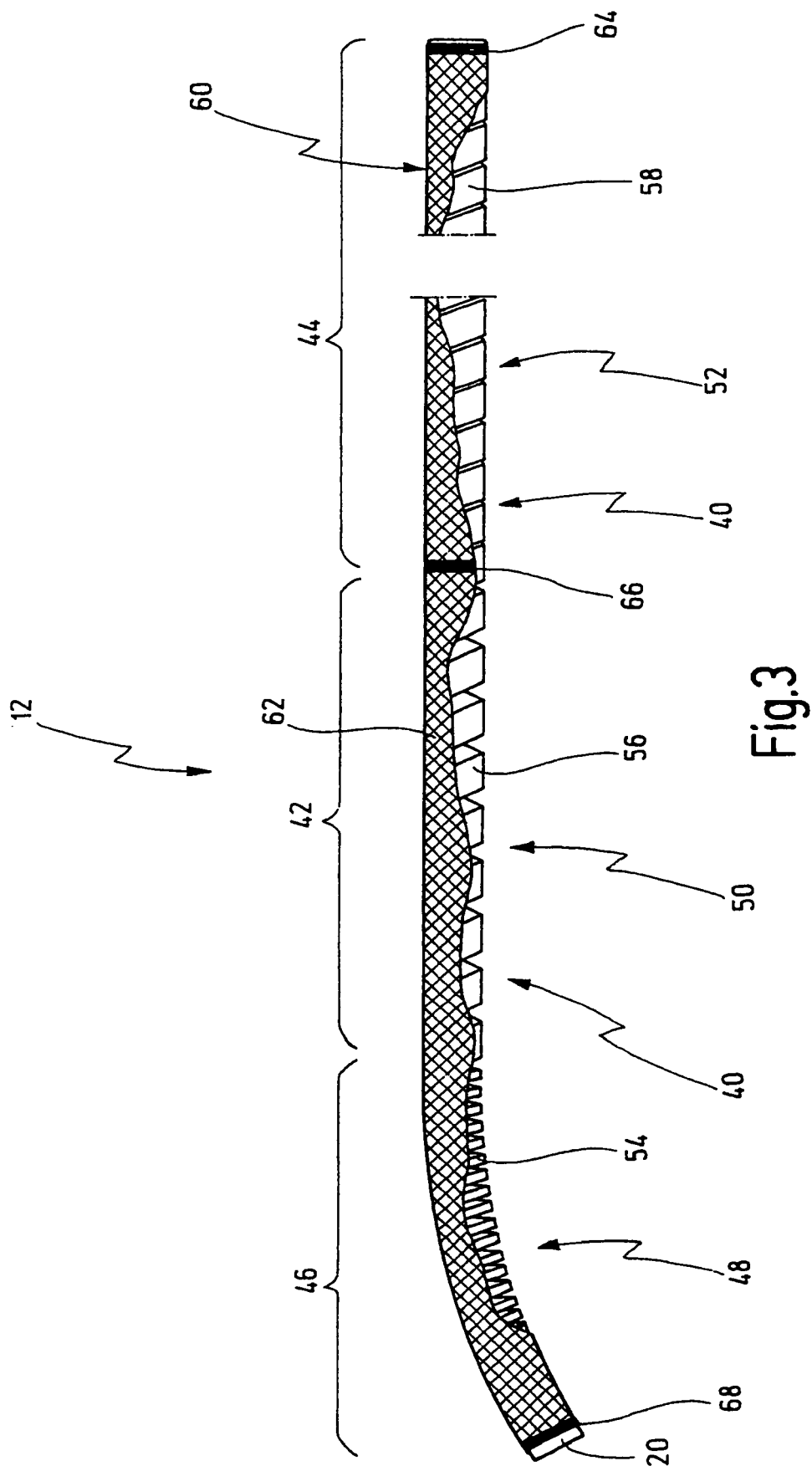
FIG. 3 shows the shaft from FIG. 2 with the outer jacket omitted.
Figure 4:
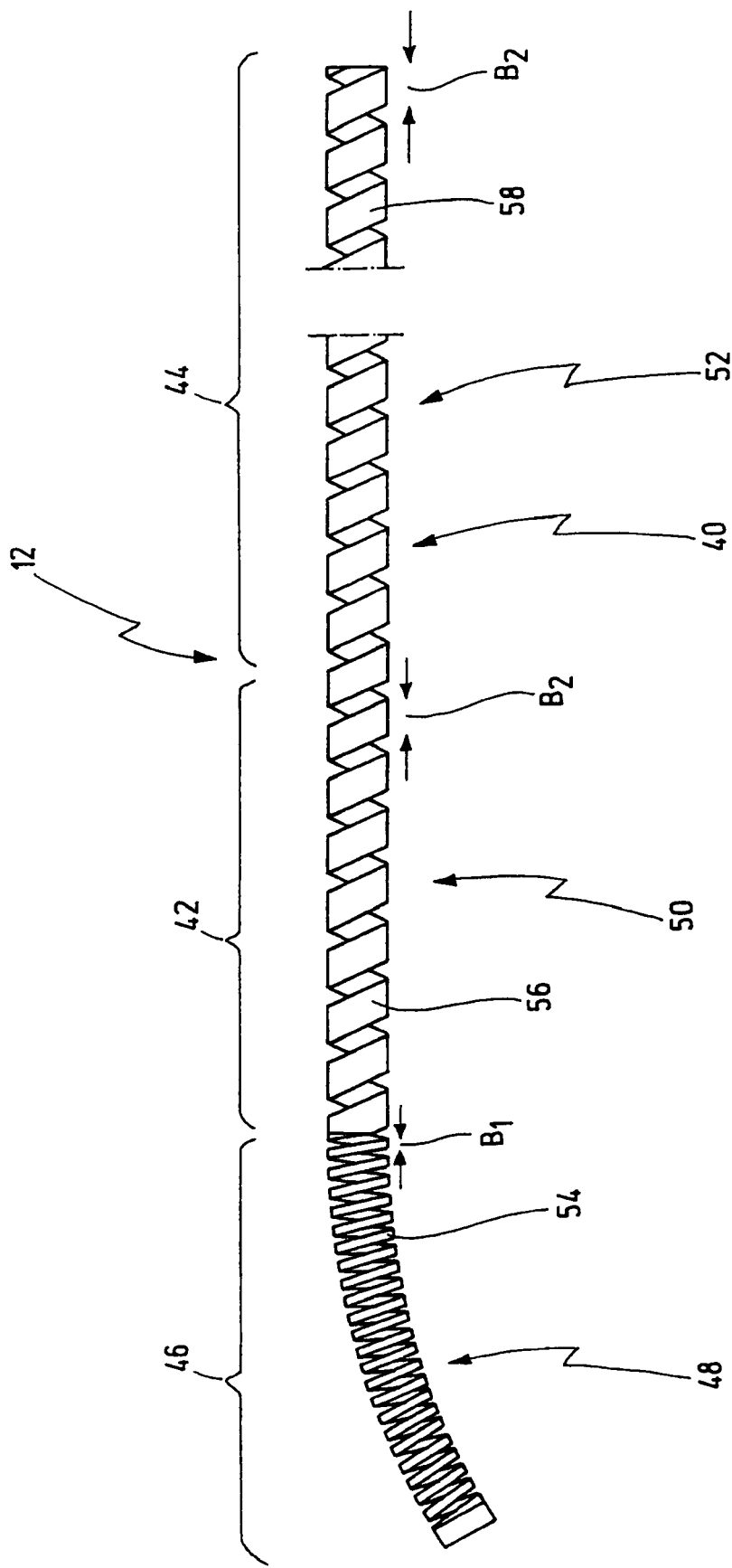
FIG. 4 shows the shaft from FIGS. 2 and 3 with the net-like sleeve element also omitted.

As will be seen from FIGS. 3 and 4, the spring elements 48, 50 and 52 are made from a strip-shaped or band-shaped flat material. The spring elements 48 to 52 can be produced from a tubular material by laser cutting.

An extent or width B1 of the individual windings 54 of the third spring element 48 is less than a width B2 of the windings 56 of the first spring element 50 and of the windings 58 of the second spring element 52. The widths B2 of the windings 56 of the first spring element 50 and of the windings 58 of the second spring element 52 are equal.

According to FIG. 3, however, despite the equal widths of the windings 56 and 58 of the first spring element 50 and of the second spring element 52, the spring hardness of the second spring element 52 is greater than the spring hardness of the first spring element 50 since the second spring element 52 according to FIG. 3 is permanently pretensioned, by means of the second spring element 52 being axially compressed, as can best be seen from FIG. 3. By means of the permanent pretensioning exerted by this compression, the flexibility in the second portion 44 of the shaft body 40 is reduced compared to the first portion 42, although, as is shown in FIG. 4, the spring elements 50 and 52 are identical if the second spring element 52 were not pretensioned.

The spring elements 48, 50 and 52 are formed integrally with one another, and, according to FIG. 4, the spring elements 50 and 52 are even portions of one and the same spring element. The spring element 48, by contrast, can be a separate spring element which is firmly connected to the first spring element 50 at the connection site, for example by laser welding.

The permanent pretensioning of the second spring element 52 is exerted by a traction element 60 which pulls the second spring element 52 axially together.

The traction element 60 is designed in the form of a net-like sleeve element 62 which is made, for example, from a thin metal tubular wire net. The sleeve element 62 extends from the distal endpiece 20 to the proximal end of the shaft 12. The net-like sleeve element 62 lies directly on the spring elements 48, 50 and 52 but is fixed to these only at certain sites, as will be described below. The sleeve element 62 is, in particular, stable against torsion.

A first attachment site 64 is located at the proximal end of the shaft body 40, specifically at the proximal end of the second spring element 52. A second attachment site 66 is located at the distal end of the second spring element 52, the distance between the attachment sites 64 and 66 corresponding to the length of the second spring element 52 in the latter's compressed state according to FIG. 3. By attaching the sleeve element 62 to the second spring element 52 at the sites 64 and 66, the sleeve element 62 accordingly applies the traction force for the permanent compression of the second spring element 52 and, consequently, the permanent pretensioning of the second spring element 52. Between the sites 64 and 66, the sleeve element 62 is not connected to the second spring element 52, so that the windings 58 of the second spring element 52 have a relative mobility with respect to the sleeve element 62 between the attachment sites 64 and 66.

A further attachment site 68 is located at the distal end of the shaft body 40, specifically on the endpiece 20. All the attachment sites 64, 66 and 68 are preferably formed as soldered connections between the metal sleeve element 62 and the metal spring elements and the metal endpiece 20.

Between the attachment sites 66 and 68, the sleeve element 62 is likewise movable relative to the windings 54 and 56 of the spring elements 48 and 50.

In the production of the shaft 12, the shaft body 40 is produced in one piece with the spring elements 48, 50 and 52 and with the endpiece 20 in accordance with FIG. 4, in which state the second spring element 52 is not as yet pretensioned. The sleeve element 62 is then pushed over the spring elements 48 to 52, for example from the direction of the endpiece 20, and, before the sleeve element 62 is fixed to the proximal end of the second spring element 52, the latter is axially compressed, after which the sleeve element 62 is secured to the second spring element 52 about its entire circumference at the attachment site 64.

Figure 2:
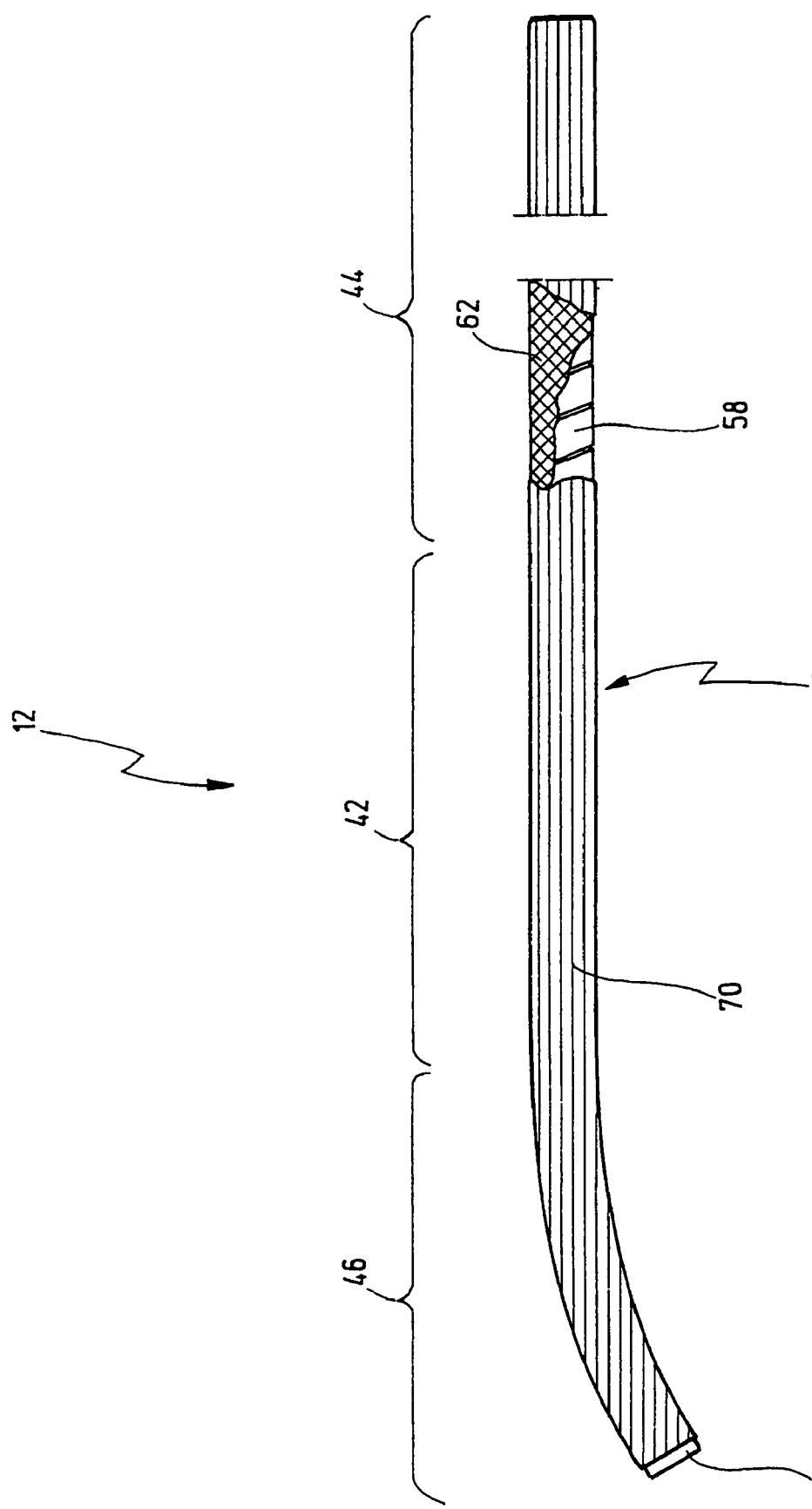
FIG. 2 shows the shaft of the endoscope from FIG. 1 on an enlarged scale and in isolation, in an interrupted view with partial sectioning.

The sleeve element 62 is in turn surrounded, according to FIG. 2, by an outer jacket 70 which likewise extends along the entire length of the shaft 12 and thus along the entire length of the sleeve element 62.

The outer jacket 70 is made of plastic and is connected to the sleeve element 62 by the action of heat, as a result of which the outer jacket 70 is connected to the sleeve element 62 with a form fit, and the shaft 12 thus has a greater torsion resistance.

What is claimed is:

1. A flexible shaft for an endoscope, comprising
a shaft body extending in a longitudinal direction, and having in said longitudinal direction a first portion with a first degree of flexibility, and, proximally from said first portion, at least a second portion with a second degree of flexibility which is less than said first degree of flexibility;
said shaft body having, in said first portion, at least a first spring element, and, in said second portion, at least a second spring element;
at least said second spring element being constructed from helical windings;
a spring hardness of said second spring element being increased by a permanent compression of said second spring element, as a result of which said second degree of flexibility of said shaft body is reduced in said second portion; and
said permanent compression of said second spring element being applied by an axial compression of said windings relative to one another, said permanent compression being applied by a net-like sleeve traction element surrounding said second spring element, said traction element pulling said windings of said second spring element axially closer together;
wherein said traction element is attached to said second spring element at two sites situated axially apart from one another, a distance between said two sites corresponding to a length of said second spring element in the compressed state of said second spring element, and wherein said net-like sleeve extends substantially over the entire length of the shaft.

2. The shaft of claim 1, wherein said sleeve element is surrounded by an outer jacket which is firmly connected to said sleeve element.

3. The shaft of claim 1, wherein said first spring element and said second spring element are formed integrally with one another.

4. The shaft of claim 1, wherein said shaft body has at least a third portion with a third degree of flexibility, said shaft body having a third spring element in said third portion, said third degree of flexibility being greater than said first degree of flexibility and greater than said second degree of flexibility.

5. The shaft of claim 4, wherein said first, second and third spring element are formed integrally with one another.

6. The shaft of claim 1, wherein said first spring element and said second spring element have the same spring hardness when said second spring element is in the non-compressed state.

7. The shaft of claim 1, wherein said first spring element and said second spring element are portions of one and the same one-piece spring element.

* * * * *